United States Patent
DesMarteau et al.

(10) Patent No.: US 6,268,532 B1
(45) Date of Patent: Jul. 31, 2001

(54) SULFONATED PERFLUOROVINYL FUNCTIONAL MONOMERS

(75) Inventors: Darryl D. DesMarteau, Clemson, SC (US); Charles W. Martin, Avondale, PA (US); Lawrence A. Ford, Greer; Yuan Xie, Clemson, both of SC (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 09/586,844

(22) Filed: Jun. 5, 2000

(51) Int. Cl.[7] .................. C07C 309/86; C07C 311/00
(52) U.S. Cl. ................. 562/828; 564/83; 564/84
(58) Field of Search .................. 562/30, 36, 41, 562/45, 46, 828; 564/82, 83

(56) References Cited

U.S. PATENT DOCUMENTS

| | | |
|---|---|---|
| 4,337,211 | 6/1982 | Ezzell et al. . |
| 4,358,412 | 11/1982 | Ezzell et al. . |
| 4,812,352 | 3/1989 | Debe . |
| 5,021,602 | 6/1991 | Clement et al. . |
| 5,023,380 | 6/1991 | Babb et al. . |
| 5,037,917 | 8/1991 | Babb et al. . |
| 5,037,918 | 8/1991 | Babb . |
| 5,037,919 | 8/1991 | Clement et al. . |
| 5,039,561 | 8/1991 | Debe . |
| 5,066,746 | 11/1991 | Clement et al. . |
| 5,159,036 | 10/1992 | Babb . |
| 5,159,037 | 10/1992 | Clement et al. . |
| 5,159,038 | 10/1992 | Babb et al. . |
| 5,162,468 | 11/1992 | Babb et al. . |
| 5,198,513 | 3/1993 | Clement et al. . |
| 5,210,265 | 5/1993 | Clement et al. . |
| 5,246,782 | 9/1993 | Kennedy et al. . |
| 5,264,508 | 11/1993 | Ishibe et al. . |
| 5,338,430 | 8/1994 | Parsonage et al. . |
| 5,364,547 | 11/1994 | Babb et al. . |
| 5,364,917 | 11/1994 | Babb et al. . |
| 5,393,852 | 2/1995 | Ishibe et al. . |
| 5,409,777 | 4/1995 | Kennedy et al. . |
| 5,426,164 | 6/1995 | Babb et al. . |
| 5,449,825 | 9/1995 | Ishibe et al. . |
| 5,620,807 | 4/1997 | Mussell et al. . |
| 5,879,828 | 3/1999 | Debe et al. . |
| 5,910,378 | 6/1999 | Debe et al. . |

FOREIGN PATENT DOCUMENTS

| | | |
|---|---|---|
| WO 97/25369 | 7/1997 | (WO) . |
| WO 99/05126 | 2/1999 | (WO) . |
| WO 99/38842 | 8/1999 | (WO) . |

OTHER PUBLICATIONS

CA:129:122975 abs of EP850920, Jul. 1998.*
CA:119:52930 abs of JP05013070, Jan. 1993.*
CA:120:284740 abs of Proc. SPIE–Int. Soc. Opt. Eng. 1911(Liquid Crystal materials, Devices and Applications II) by Perettie et al pp 15–20, 1993.*

* cited by examiner

Primary Examiner—Jean F. Vollano
(74) Attorney, Agent, or Firm—Philip Y Dahl

(57) ABSTRACT

The present invention provides a monomer having the formula A—B, wherein A is represented by Formula I:

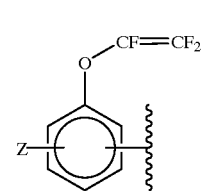

(I)

wherein B is selected from —OCF=$CF_2$ and —A; wherein, when B is —OCF=$CF_2$, the orientation of B is meta or para to the trifluorovinyloxy group of A; wherein, when B is A, the bond joining the A groups is para to the trifluorovinyloxy group of each A; and wherein each Z is independently selected from —$SO_2F$, —$SO_2Cl$, —$SO_3H$, —$SO_2$—N(M)—$SO_2CF_3$, and —$SO_2$—N(M)—$SO_2R_f$; wherein M is any suitable cation and $R_f$ is a C1 to C10 fluorocarbon or fluorinated ether group.

The present invention also provides a monomer according to Formula II:

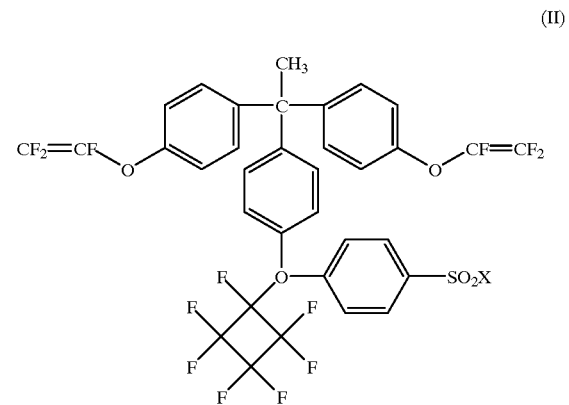

(II)

wherein X is F, Cl, or N(M)$SO_2R_f$, wherein M is any suitable cation and $R_f$ is a C1 to C10 fluorocarbon or fluorinated ether group.

11 Claims, No Drawings

SULFONATED PERFLUOROVINYL FUNCTIONAL MONOMERS

TECHNICAL FIELD

This invention relates to sulfonated perfluorovinyl monomer compositions, methods for making same, and polymers made from them.

BACKGROUND

Perfluorinated allyl vinyl ethers have been described, for example in U.S. Pat. No. 4,337,211 that describes alkyl fluorocarbon ethers and methods for preparation thereof, and U.S. Pat. No. 4,358,412 that describes methods for preparation of alkyl vinyl ether monomers.

U.S. Pat. No. 5,264,508 describes polymers and copolymers prepared from diunsaturated mono- or poly-perfluoro or haloperfluoro ethers. One site of unsaturation is used in the polymerization, resulting in a melt-processable polymer. The second site of unsaturation is then available to crosslink the polymer giving a thermoset polymer. The copolymerization monomers said to be useful include "virtually any ethylenically unsaturated monomer capable of polymerization." (col. 5 lines 31–32). Phenyl and naphthyl radicals may be included in an ether used in the copolymerization, and these radicals may include substituent groups such as a halogen or —SO$_2$F.

U.S. Pat. No. 5,449,825 describes a method of preparation of perfluoro and haloperfluoro ethers, diethers and polyethers containing vinyl unsaturation, or allyl and vinyl unsaturation.

U.S. Pat. No. 5,023,380 describes compounds having two or more perfluorovinyl groups, along with their polymerization. Sulfur and sulfur-containing groups may be in the backbone of these materials. A hydrocarbyl group in the backbone must be either unsubstituted or inertly substituted, which is said to include sulfide, sulfoxide, and sulfone.

U.S. Pat. No. 5,066,746 describes a process of preparing tris-perfluorovinylether monomers.

WO 99/38842 describes perfluorovinylbenzene sulfonyl fluoride as a precursor to a polymer. It also describes polyimide-type aromatic polymers of sulfonated sulfone polyethers, and mono- and bi-functional monomers that can have sulfur-containing backbones or substituents.

WO 97/25369 describes several composite membranes that include various trifluorostyrene, substituted trifluorostyrene, and ethylene-based monomers.

WO 99/05126 describes perfluorovinyl ionic compounds and polymers made using them. The formulas described include perfluorovinyloxy substituents on a pentacyclic group and a backbone containing an aromatic group having one or more substitutents in addition to a sulfonyl group.

The polymerization of trifluorovinyl-containing monomers to form perfluorocyclobutylene polymers has been disclosed. For example, U.S. Pat. Nos. 5,037,917 and 5,066,746 describe a thermal process for preparing a polymer containing perfluorocyclobutane rings. The typical monomers described in these references have at least two dimerizable perfluorovinyl groups.

SUMMARY OF THE INVENTION

Briefly, the present invention provides a monomer having the formula A—B, wherein A is represented by Formula I:

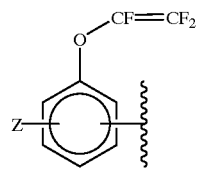

(I)

wherein B is selected from —OCF=CF$_2$ and —A;
wherein, when B is —OCF=CF$_2$, the orientation of B is meta or para to the trifluorovinyloxy group of A;
wherein, when B is A, the bond joining the A groups is para to the trifluorovinyloxy group of each A; and
wherein each Z is independently selected from —SO$_2$F, —SO$_2$Cl, —SO$_3$H, —SO$_2$—N(M)—SO$_2$CF$_3$, and —SO$_2$—N(M)—SO$_2$R$_f$; wherein M is any suitable cation and R$_f$ is a C1 to C10 fluorocarbon or fluorinated ether group.

The present invention also provides a monomer according to Formula II:

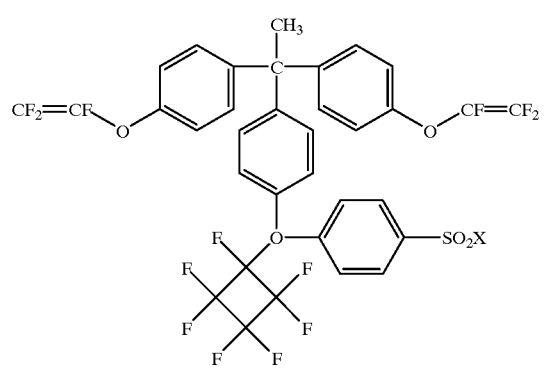

(II)

wherein X is F, Cl, or N(M)SO$_2$R$_f$, wherein M is any suitable cation and R$_f$ is a C1 to C10 fluorocarbon or fluorinated ether group.

In this document "substituted" when used without reference to a particular substituent, means substituted by conventional substituents which do not interfere with the desired product or process, e.g., substituents can be alkyl, alkoxy, aryl, phenyl, halo (F, Cl, Br, I), cyano, nitro, etc. Also, "C(number)" refers to a chemical moiety containing the indicated number of carbon atoms.

These monomers are useful in preparing polymers such as described in copending U.S. patent application Ser. No. 09/589,522. Such polymers can have desirable mechanical properties along with a desirable level of ionic conductivity. For example, block copolymers having sulfonated and non-sulfonated blocks can be prepared. By controlling the block proportions of sulfonated monomer, the ionic conductivity of the resultant polymer can be controlled. By controlling the block proportions of one or more other monomers, the mechanical properties of the resultant polymer can be controlled.

DETAILED DESCRIPTION OF PREFERRED EMBODIMENTS

The present invention provides perfluorovinyl monomers comprising sulfonated units and methods for making them. The present invention also provides polymers comprising the monomers having sulfonated units. These monomers have at least two trifluorovinyloxy groups that are attached to one or more aryl groups.

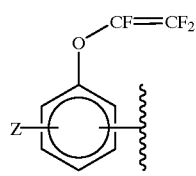
(I)

The general form of the monomers of the present invention is A—B. The first portion, A, is represented by Formula I, shown above, with an open valence to a B group. Thus, A includes a core aryl group with a trifluorovinyloxy group and a separate group defined by Z.

B is either —OCF=$CF_2$, or a second A group. When B is a second trifluorovinyloxy group, the core aryl group has two trifluorovinyloxy substituents that are either meta or para to each other. When B is a second A group, the trifluorovinyloxy group of each A group is para to the bond connecting the two A groups.

Z is independently selected from sulfur-containing subgroups, for example, —$SO_2$F, —$SO_2$Cl, —$SO_3$H, —$SO_2$—N(M)—$SO_2CF_3$, and —$SO_2$—N(M)—$SO_2R_f$, wherein M is any suitable cation and $R_f$ is a C1 to C10 flurorocarbon or fluorinated ether group. The choice of which particular group for each Z and the orientation of each Z group are independently selected. Generally, Z is ortho or meta to the —OCF=$CF_2$ group of portion A.

M is any suitable cation, such that it does not interfere with polymerization and that it is exchangeable with other cations, particularly $H^+$. Examples include $H^+$, alkali metals, and $R_4N^+$ where $R_4$ is a C1–C10 saturated alkyl group.

$R_f$ can be any suitable C1 to C10 fluorocarbon or fluorinated ether group. Examples include fluorocarbons having the formula $C_nF_{2n+1}$ wherein n is an integer from 1 through 10. Examples of fluorinated ether groups include $CF_3(CF_2)_y OCF_2CF_2$—, wherein y is an integer from 1 through 7, and $R_k$—$CH_2OCF_2CF_2$—, wherein $R_k$ is $CF_3$ or $C_mF_{2m+1}$ with m being an integer from 1 through 7.

Another monomer of the present invention comprises a reaction product of a tris(trifluorovinyloxy aryl) alkane, such as 1,1,1-tris(4'-trifluorovinyloxyphenyl)ethane, and a sulfonated trifluorovinyloxyaryl monomer.

Any suitable reaction conditions and equipment may be used to prepare the monomers of the present invention, including batch or continuous processes. Suitable conditions and equipment disclosed in the examples section below may be used. Generally, a base material having the target phenyl groups is reacted to replace the hydrogen on the substituent phenyls with an alkali metal. Then a halo-tetrafluoro alkane is substituted for the alkali metal. The halotetrafluoroalkane-substituted intermediate is then sulfonated, such as with a halosulfonic acid. This reaction product is neutralized, dried, and purified. Then the material is fluorinated by substituting fluorine for the halo in the halosulfonic acid substituent. Finally, a dehalogenation process converts the halotetrafluoroalkane substituent to the desired trifluorovinyloxy group.

The monomers of the present invention may be polymerized by any suitable method. Polymerization involves joining trifluorovinyl groups of the monomer molecules to form linking perfluorocyclobutylene (PFCB) groups. In addition, the monomers of the present invention may be copolymerized with any suitable co-monomer or co-monomers. Heating is a preferred method of polymerization of the monomers or monomer mixtures.

Desirable properties may be obtained by controlling the relative amounts of the sulfonated monomer or monomers and non-sulfonated monomers. Higher quantities of sulfonated monomer tend to result in higher ionic conductivity in the resultant polymer, at the expense of lower mechanical properties. By including non-sulfonated monomers, such as di(trifluorovinyloxy)aromatic monomers, $CF_2$=CFO—Ph—OCFC=$F_2$, ($CF_2$=CFO—Ph—$)_2$, and 1,1,1-tris(4'-trifluorovinyloxyphenyl)ethane, the electrical and mechanical properties of the polymer can be targeted for a particular use. These monomers are therefore useful in preparing polymers having properties desirable for ion-exchange membranes.

The versions of the invention described above have many advantages, including controlled mechanical and electrical properties.

EXAMPLES

Example 1

This example illustrates the preparation of a monomer of the present invention.

Preparation of 4,4'-di(2-bromoterafluoroethoxy)biphenyl

A solution of 28.7 g (0.15 mol) of 4,4'-bisphenol in 75 mL of DMSO was placed into a 500 mL round-bottom flask. The solution was purged with nitrogen gas at room temperature (23° C.) for 2–3 hours. Then, 140.85 mL of 2.13M (0.300 mol) of standardized aq KOH was added dropwise to the solution in the flask, while the flask rested in an ice-bath and the nitrogen gas purge continued. After the KOH solution was added, the reaction mixture was heated to 100° C. and stirred for 1 day, followed by distilling off most of the water. The remaining solvent was evaporated off slowly under reduced pressure (10 torr). The reaction product was then dried thoroughly at 140–150° C. with fill vacuum ($10^{-2}$ torr) for at least 2 days. Then, a solution of 104 g (0.4 mol) of 1,2-dibromotetrafluoroethane in 100 mL of well-dried DMSO was transferred to the flask via a closed system. The mixture was stirred at 35–40° C. for 4 days, followed by filtration to remove the solid precipitate. The precipitate was washed with acetone three times. The combined acetone solution was then washed in a separatory fimnel, first with a 5% sodium bicarbonate water solution, then with 0.1N HCl, and finally washed with distilled water and dried over sodium sulfate overnight. After removing solid material by filtration and evaporating the solvents at reduced pressure (10 torr), the crude product was purified by sublimation with an oil bath at a temperature around 100–110° C. A product of 75 g (0.137 mol) of 4,4-di(2-bromotetrafluoroethoxy) biphenyl was obtained at a yield of 91%. The amount of hydrogen by-product in the fmal product was around 1%.

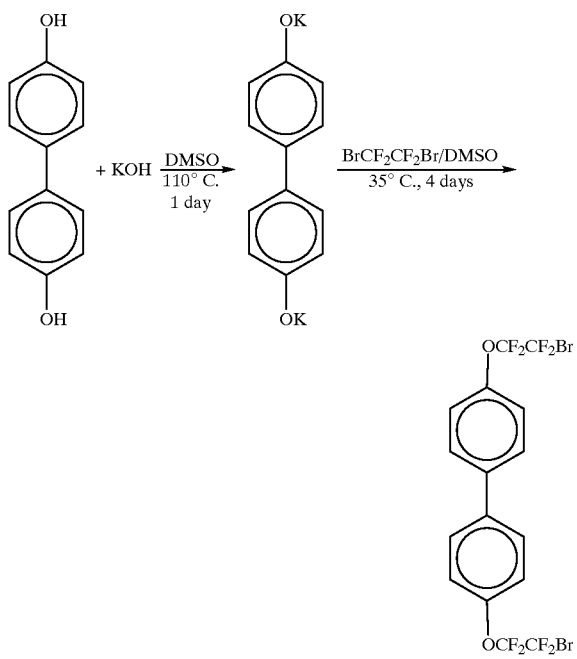

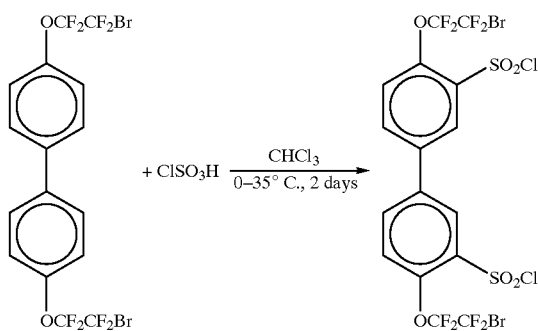

Sulphonation of 4,4-di(2-bromotetrafluoroethoxy)biphenyl

A sample of 70.72 g (0.13 mol) of 4,4'-di(2-bromotetrafluoroethoxy)biphenyl was dissolved in 250 mL of chloroform. The solution was placed into a 1 L round-bottom flask resting in an ice bath. To this solution, 500 g of chlorosulfonic acid was added dropwise. After the initial evolution of hydrochloric acid had subsided, the reaction solution was brought to 35–40° C. and stirred for 2 days under nitrogen gas. The contents of the flask were poured into a 2 L beaker filled with crushed ice, the chloroform layer was separated and washed with ice water. After drying over sodium sulfate, the crude product was purified by recrystallization using chloroform as solvent. A yield of 92% was obtained, resulting in 90 g (0.12 mol) of 4,4'-di(2-bromotetrafluoroethoxy)-3,3'-biphenyldisulfonyl chloride. The amount of hydrogen by-product in the final product was below 1%.

Fluorination of 4,4'-di(2-bromotetrafluoroethoxy)-3,3'-biphenyldisulfonyl chloride Into a 500 mL round bottom flask were placed 35 g (0.047 mol) of the 4,4'di(2-bromotetrafluoroethoxy)-3,3'-biphenyldisulfonyl chloride and 21.8 g (0.38 mol) of freshly fused potassium fluoride powder. Then, 200 mL of well dried acetonitrile was added to the flask and the mixture was refluxed under dry nitrogen for 2 days, followed by filtration to remove the solid material. This solid was then washed with acetone three times. The combined organic layer was washed in a 500 mL separatory funnel with saturated sodium chloride water solution three times and dried over sodium sulfate overnight. After the removal of solid materials by filtration and the evaporation off the solvents, the crude product of 4,4'-di(2-bromotetrafluoroethoxy)-3,3'-biphenyldisulfonyl fluoride was purified by recrystallization using chloroform.

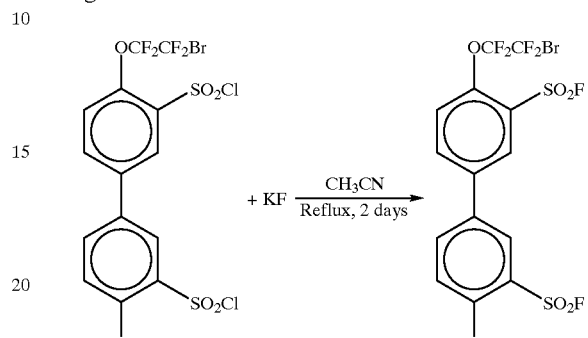

Preparation of 4,4'-di(trifuorovinyloxy)-3,3'-biphenyldisulfonyl fluoride

Into a 500 mL of round-bottom flask in a dry box were placed 19.62 g (0.0277 mol) of the 4,4'-di(2-bromotetrafluoroethoxy)-3,3'-biphenyldisulfonyl fluoride, along with 5.56 g (0.05 mol) of copper(I) chloride and 6.5 g (0.1 mol) of activated zinc powder. Then, 120 mL of well-dried acetonitrile was added to the flask. The mixture was stirred at 110° C. under dry nitrogen for 4 days, followed by taking a sample for $^{19}F$ NMR to monitor the progress of the reaction. The spectrum of this sample showed that the dehalogenation reached its completion. After cooling the reaction mixture, the solution was filtered to remove the solid materials and the filtrate was diluted with 150 mL of methylene chloride, and refluxed with active carbon overnight. After filtration and evaporation of the solvents, the crude product was purified by column chromatography (silica gel, 70–230 mesh, from Aldrich Chemical Co.) using 2 parts by volume petroleum ether to 1 part by volume chloroform as eluant. The product was 4,4'-di(trifluorovinyloxy)-3,3'-biphenyldisulfonyl fluoride.

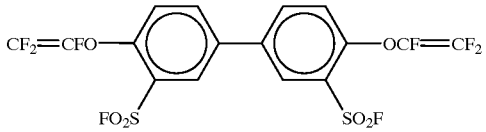

Example 2

This example illustrates the preparation of a monomer of the present invention.

Preparation of 2,5-di(2-bromotetrafluoroethoxy) benzenesulfonic acid, potassium salt First, 9.80 g (0.0434 mol) of 2,5-dihydroxybenzene sulfonic acid, potassium salt was dissolved in 45 mL of DMSO, and the solution was purged with nitrogen gas for 2–3 hours. Then 40.34 mL of 2.15M KOH water solution (0.0868 mol) was added to the solution dropwise with the reaction vessel resting in an ice-bath and under nitrogen gas. After finishing the addition of KOH solution, the reaction mixture was brought to 100° C. and stirred for one day. Most of water was recovered by distillation and the remaining solvents were evaporated away slowly under the reduced pressure (10 torr). The salt was dried thoroughly at 130° C. under fall vacuum ($10^{-2}$ torr) for 2 days. The dried salt and 80 mL of dry DMSO were transferred to a 250 mL stainless steel cylinder containing a stirring bar in a dry box, followed by transferring 62.4 g (0.24 mol) of 1,2-dibromotetrafluoroethane via vacuum line to the cylinder. The mixture was stirred at 50° C. for 4 days. Then, the cylinder was cooled to room temperature (23° C.), and the contents of the cylinder were poured into a 100 mL beaker. A sample of bulk solution was taken for $^{19}F$ NMR; the spectrum of this sample showed that the reaction at nearly 40% conversion and the amount of hydrogen by-product was about 4.8%. The bulk solution was filtered and tested as neutral at this stage. The solid materials were washed with acetone and the filtrate was diluted with 120 mL of methylene chloride. The combined organic layer was washed with a saturated NaCl-water solution in a 500 mL separatory funnel and dried over sodium sulfate overnight. After removal of drying agent by filtration and evaporation of solvents, a sample of crude product was taken for $^{19}F$ and $^1H$ NMR. The spectrum of this sample showed that there was some DMSO in the product. After sampling, 11 g of the crude product of 2,5-di(2-bromotetrafluoroethoxy) benzenesulfonic acid, potassium salt material was obtained.

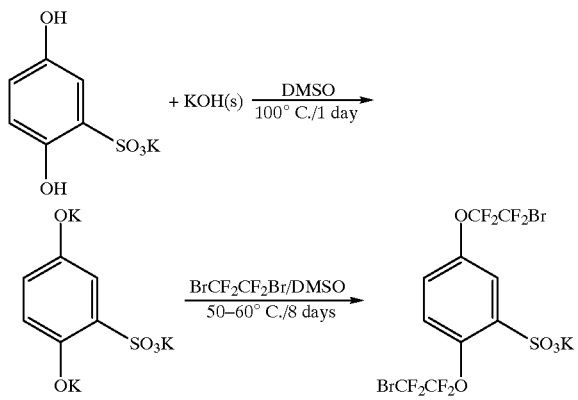

Chlorination of 2,5-di(2-bromotetrafluoroethoxy) benzenesulfonic acid, potassium salt A mixture of 5.86 g (0.01 mol) of the 2,5-di(2-bromotetrafluoroethoxy) benzenesulfonic acid, potassium salt, 10 mL acetonitrile, 10 mL sulfolane and 6 mL phosphoryl chloride was placed into a 100 mL round-bottom flask, and stirred at 68–82° C. for 1 hour. The mixture was then cooled down to below 5° C. (with the reaction vessel resting in an ice-bath) and 15 mL ice-cold water was added dropwise. Stirring was continued at a temperature below 10° C. for 20 minutes and the precipitated oily product was isolated by suction and then diluted with 100 mL of methylene chloride. The combined organic layer was washed with saturated aq. sodium chloride in a 500 mL separatory funnel until neutral and dried over sodium sulfate overnight. After the removal of the salt by filtration and the evaporation of the solvents, the crude product was purified by distillation at reduced pressure (10 to $10^{-2}$ torr) to collect 102–106° C. fraction at vacuum. A total of 5.00 g (0.0088 mol) of 2,5-di(2-bromotetrafluoroethoxy) benzenesulfonyl chloride was obtained in 88.2% yield.

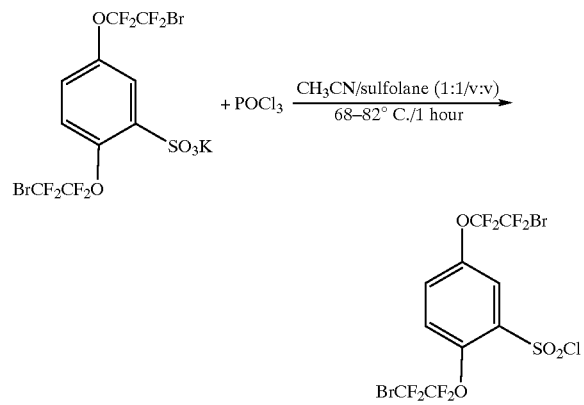

Fluorination of 2,5-di(2-bromotetrafluoroethoxy) benzenesulfonyl chloride

Into a 100 mL round-bottom flask in a dry box were added: 5.00 g (0.0088 mol) of 2,5-di(2-bromotetrafluoroethoxy) benzenesulfonyl chloride, 2.04 g (0.0352 mol) of freshly fused potassium fluoride powder, and 30 mL of dry acetonitrile. The mixture was refluxed for 2 days under nitrogen gas. After being cooled to room temperature (23°), the reaction solution was filtered to remove the solid materials, which were then washed twice with acetone. The solution was diluted with 150 mL of methylene chloride and the combined organic layer was washed with saturated aq. sodium chloride three times and dried over sodium sulfate overnight. The crude product was purified by distillation at reduced pressure (10 to $10^{-2}$ torr) to collect 92–95° C. fraction at vacuum. A total of 3.76 g (0.0068 mol) of 2,5-di(2-bromotetrafluoroethoxy) benzenesulfonyl fluoride was obtained in 77.7% yield. The product contained 13% of the starting material.

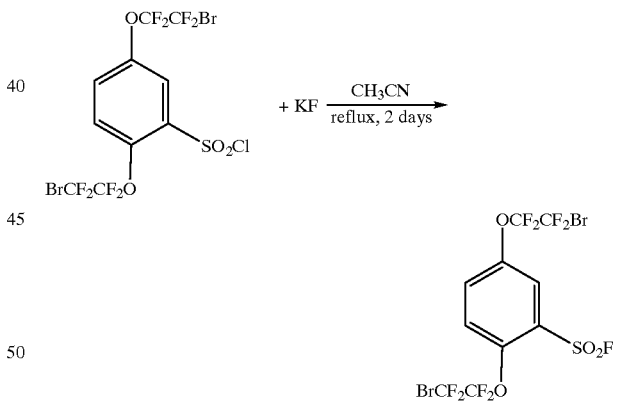

Preparation of 2,5-di(trifluorovinyloxy) benzenesulfonyl fluoride

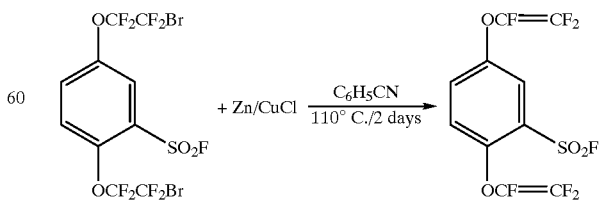

Into a 250 mL round-bottom flask were placed 16.5 g (0.03 mol) of 2,4-di(2-bromotetrafluoroethoxy) benzenesulfonyl fluoride, 5.94 g (0.06 mol) of copper(I) chloride and 6.54 g (0.1 mol) of activated zinc powder, and 120 mL of well-dried benzonitrile was added to the mixture. The solution was stirred at 110° C. for 2 days under dry nitrogen gas. After cooling to room temperature, the reaction mixture was diluted with 120 mL of methylene chloride and the mixture was stirred at that temperature for eight hours, followed by filtration to remove the solid materials. Then, 5 g of active carbon was added to the filtrate and the mixture was refluxed for overnight. After cooling to room temperature, the mixture was filtered to remove active carbon and the solvents were removed under reduced pressure. The crude product was purified by sublimation at 120° C. oil bath temperature at $10^{-2}$ torr. The sublimed material was 2,5-di(trifluorovinyloxy) benzenesulfonyl fluoride.

Example 3

This example illustrates the preparation of a monomer of the present invention.

Preparation of 1,3-di(2-bromotetrafluoroethoxy)benzene

Into a 250 mL round-bottom flask were placed 18.72g (0.17 mol) of 1,3-dihydroxybenzene (resorcinol) and 75 mL of DMSO. The solution was purged with nitrogen gas for one hour followed by adding 223.62 mL of 1.52M (0.34 mol) KOH-water solution dropwise to the solution, with the reaction flask resting in an ice-bath. The reaction mixture was then heated at 100° C. for one day followed by distilling off most of the water from the reaction solution. The rest of reaction solvents were evaporated slowly under vacuum. The salt was dried at 120° C. under the vacuum line for at least two days. Then 75 mL of dry DMSO and 109.2 g (0.42 mol) of 1,2-dibromo tetrafluoroethane was transferred to the flask via a closed system. The mixture was stirred at 35° C. for 3 days. The reaction mixture was filtered to remove the KBr, then the reaction mixture was washed with acetone in a 500 mL separatory funnel and the organic layer was diluted with 150 mL of methylene chloride. The combined organic layer was washed first with 10% of sodium bicarbonate water solution, and then with 0.01N HCl and finally with distilled water until neutral. The solution was dried over sodium sulfate overnight. After the removal of the sodium sulfate by filtration and the evaporation of the solvents, the crude product was purified by distillation under reduced pressure with an oil bath at a temperature of 100–110° C. A total of 64 g (0.136 mol) of 1,3-di(2-bromotetrafluoroethoxy)benzene was obtained in 80.4% yield, which had a boiling point of 76–80° C. (at $10^{-2}$ torr). The amount of hydrogen by-product in the product was about 5.4%.

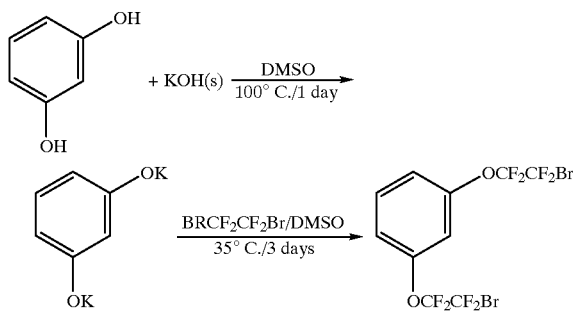

Chlorination of 1,3-di(2-bromotetrafluoroethoxy)benzene

In a 250 mL of round-bottom flask resting in an ice-bath were placed 23.35 g (0.05 mol) of this 1,3-di(2-bromotetrafluoroethoxy)benzene and 100 mL of chloroform. Then 116 g of chlorosulfonic acid was added dropwise into the solution. After the initial evolution of hydrogen chloride had subsided, the mixture was brought to room temperature. The reaction mixture was stirred at room temperature for 1 hour, then heated at 35° C. for another day. The contents of the flask were poured into a 1 L beaker filled with crushed ice. The chloroform layer was separated and washed with ice cold water to neutral. The organic layer was dried over sodium sulfate. After the removal of the solid materials by filtration, the chloroform was evaporated off completely. The crude product was purified by distillation under the reduced pressure to collect the fraction boiling at 127–129° C./$10^{-2}$ torr. A total of 25.1 g (0.0443 mol) of 2,4-bis(2-bromotetrafluoroethoxy)benzenesulfonyl chloride was obtained in 88.7% yield. The quantity of hydrogen by-product was below 3%.

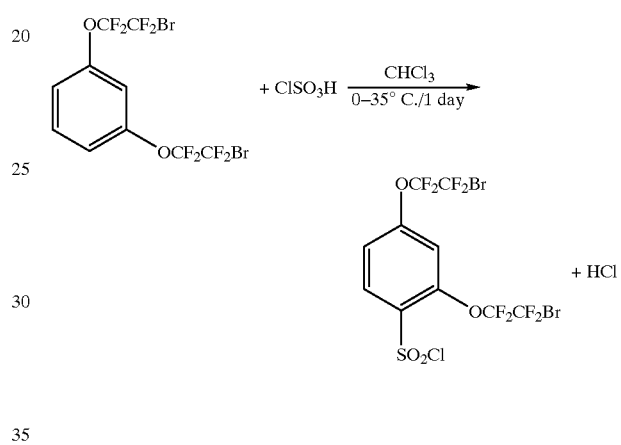

Fluorination of 2,4-di(2-bromotetrafluoroethoxy) benzenesulfonyl chloride

To a 250 mL round-bottom flask were added 24.5 g (0.0432 mol) of 2,4-di(2-bromotetrafluoroethoxy) benzenesulfonyl chloride and 10.00 g (0.173 mol) of freshly fused potassium fluoride in a dry box, followed by adding 100 mL of well-dried acetonitrile. The mixture was stirred at reflux for two days. After removal of solid materials by filtration, the reaction mixture was diluted with 150 mL of methylene chloride and washed with saturated aq. sodium chloride three times. The organic layer was dried over sodium sulfate overnight. After removal of all solids and liquids, the crude product was purified by distillation under reduced pressure to collect a fraction boiling at 102–104° C./$10^{-2}$ torr. A total of 18.80 g (0.0342 mol) of 2,4-di(2-bromotetrafluoroethoxy)benzenesulfonyl fluoride was obtained in 79.2% yield. The amount of hydrogen by-product in this product remained at 3%.

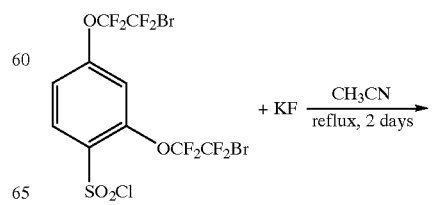

Preparation of 2,4-di(trifluorovinyloxy)benzenesulfonyl fluoride

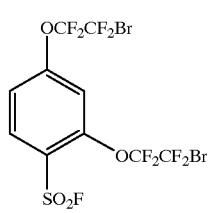

Into a 250 ml of round bottom flask were placed 16.5 g (0.03 mol) of the 2,4-di(2-bromotetrafluoroethoxy) benzenesulfonyl fluoride, 5.94 g (0.06 mol) of copper(I) chloride and 6.54 g (0.1 mol) of activated zinc powder. Then 120 mL of well-dried benzonitrile was added to the mixture. The solution was stirred at 110° C. for 2 days with the protection of dry nitrogen gas. After being cooled down to room temperature, 120 mL of methylene chloride was added to the flask and the mixture was stirred at that temperature for eight hours, followed by filtration to remove the solid materials. Then 5 g of active carbon was added to the filtrate and the mixture was refluxed for overnight. After being cooled down to room temperature, the mixture was filtered to remove active carbon and the solvents were removed under the reduced pressure. The crude material was purified by sublimation at 120° C. oil bath temperature at $10^{-2}$ torr to give 2,4-di(trifluorovinyloxy) benzenesulfonyl fluoride, identified by $^{19}F$ and $^1H$ NMR.

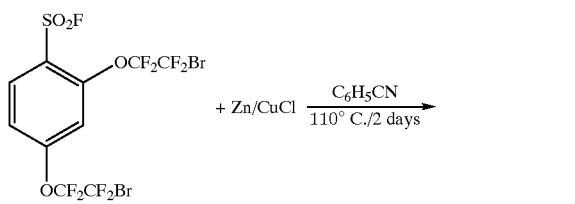

Example 4

This example illustrates the preparation of a monomer of the present invention.

Preparation of Percursor 4A

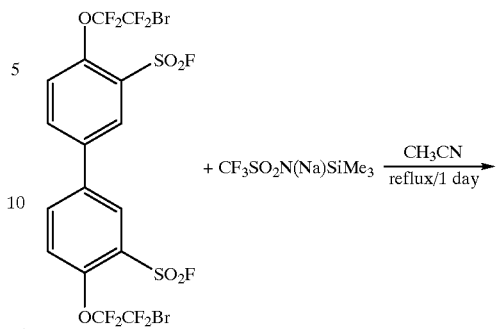

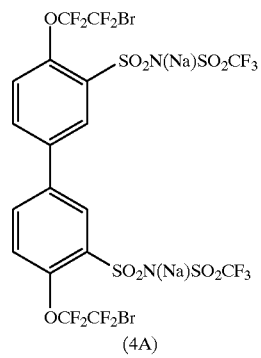

Into a 50 mL round-bottom flask in a dry box were added 1.42 g (0.002 mol) of 4,4'-di(2-bromotetrafluoroethoxy)-3, 3'-benzenedisulfonyl fluoride and 0.462 g (0.0042 mol) of $CF_3SO_2N(Na)SiMe_3$, followed by adding 25 mL of well dried acetonitrile. The mixture was refluxed under dry nitrogen gas for one day followed by evaporating the solvent completely under reduced pressure of 10 torr. The crude product was purified by first acidification, and then vacuum sublimation ($10^{-2}$ torr) to remove the excess $CF_3SO_2NH_2$ and finally converted back to its salt form by neutralization with 0.20M NaOH. A total of 1.92 g (0.0019 mol) of precursor 4A was obtained as white solid in 95% yield after removing water at $10^{-2}$ torr while heating at 100° C.

Debromination of Precursor 4A

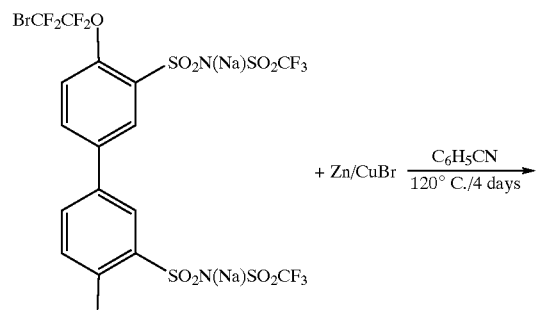

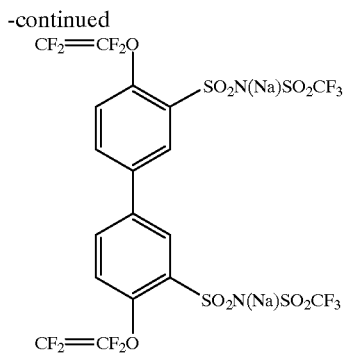

Into a 100 mL round-bottom flask in a dry box were added 1.62 g (0.0016 mol) of compound 4A and 0.655 g (0.01 mol) of well-activated zinc powder and 1.43 g (0.1 mol) of copper bromide followed by adding 50 mL of well-dried benzonitrile. The mixture was stirred at 120° C. in a closed system for four days. A sample was taken for $^{19}F$ NMR, the spectrum of which showed that the dehalogenation reaction had reached its completion. The mixture was cooled to room temperature and filtered to remove solid materials, after which benzonitrile was evaporated off completely. The remaining material was diluted with 75 mL of methylene chloride and refluxed with active carbon overnight. After filtration to remove active carbon and evaporation of the solvent, the crude product was purified by column chromatography (silica gel, 70–230 mesh) using 2 parts by volume of petroleum ether to 1 part by volume of chloroform.

Example 5

This example illustrates the preparation of a monomer of the present invention.

Preparation of 3,5-di(2-bromotetrafluoroethoxy) benzenesulfonic acid, sodium salt A sample of 3,5-dihydroxybenzene sulfonic acid sodium salt was dried at 130° C/full vacuum for two days to the form of sodium salt dihydrate: 3,5-$(HO)_2C_6H_3SO_3Na$—$2H_2O$. A sample of 4.90 g (0.0217 mol) of the dried material were dissolved in 20 mL of DMSO, and the solution was purged with nitrogen gas for 2–3 hours. Then 20.17 mL of 2.15M KOH-water solution(0.0434 mol) was added to the solution dropwise with the reaction vessel resting in an ice-bath and under nitrogen gas. After addition of KOH solution, the reaction mixture was brought to 100° C. and stirred for one day. Most of the water was recovered by distillation and the remaining solvents were evaporated slowly under reduced pressure. The salt was dried thoroughly at 130° C./at $10^{-2}$ torr vacuum for 2 days. The dried salt and 40 mL of dry DMSO were transferred to a 250 mL stainless steel cylinder containing a stirring bar in dry box, followed by transferring 20.8 g (0.08 mol) of 1,2-dibromotetrafluoroethane via vacuum line to the cylinder. The mixture was stirred at 50° C. for 4 days. The cylinder was cooled to room temperature, and the contents of the cylinder were poured into a 100 mL beaker. A sample of bulk solution was taken for $^{19}F$ NMR, the spectrum of this sample showed that the reaction conversion was nearly 40% and the amount of hydrogen by-product was about 5.8%. The bulk solution was filtered and tested as neutral at this stage. The solid materials were washed with acetone and the filtrate was diluted with 120 mL of methylene chloride. The combined organic layer was washed with saturated aq. sodium chloride and dried over sodium sulfate overnight. After the removal of drying agent by filtration and the evaporation off the solvents under vacuum of $10^{-2}$ torr at 100° C., a sample of crude product was taken for $^{19}F$ and $^{1}H$ NMR. The spectra of this sample showed that there was DMSO still in the product. A total of 5 g of product containing 3,5-di(2-bromotetrafluoroethoxy) benzenesulfonic acid, sodium salt was obtained.

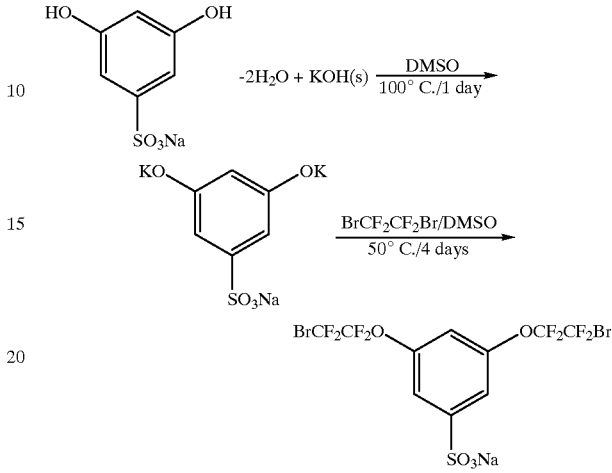

Chlorination of 3,5-di(2-bromotetrafluoroethoxy) benzenesulfonic acid, sodium salt A mixture of 3,5-di(2-bromotetrafluoroethoxy) benzenesulfonic acid, sodium salt (2.85 g of sample from preceding reaction), 15 mL of acetonitrile and 6 mL of phosphoryl chloride were placed into a 100 mL round-bottom flask, and the mixture was stirred at reflux for 1 hour. The mixture was then cooled to below 5° C. (resting the reaction vessel in an ice-bath) and 10 mL of ice water was added dropwise to the solution. Stirring was continued at a temperature below 10° C. for 20 minutes, and the precipitated oily product was isolated by suction and diluted with 100 mL of methylene chloride, washed with saturated sodium chloride water solution in a 500 mL separatory funnel until neutral. The combined organic layer was dried over sodium sulfate overnight. The crude product was purified by distillation under reduced pressure to collect the fraction boiling at 105–108° C./$10^{-2}$ torr. A total of 2.12 g of transparent, oily product was obtained. The $^{1}H$ NMR spectrum of this 3,5-di(2-bromotetrafluoro ethoxy) benzenesulfonyl chloride product indicated essentially pure product.

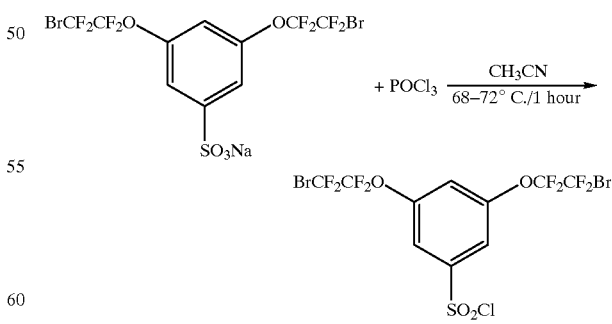

Preparation of 3 5-di(2-bromotetrafluoroethoxy) benzenesulfonyl fluoride

Into a 500 mL round bottom flask in a dry box were placed 27.5 g of 3,5-di(2-bromotetrafluoroethoxy)benzenesulfonyl chloride (obtained from the above reaction)

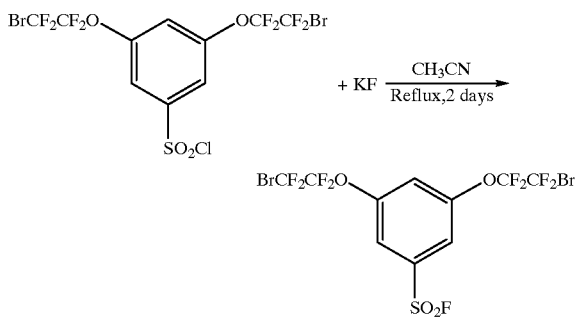

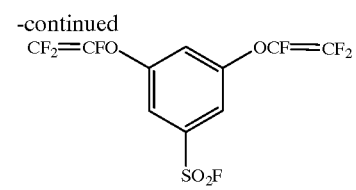

and 17.0 g of freshly fused KF powder. Then 200 mL of well-dried acetonitrile was added to the flask and the mixture was refluxed under nitrogen gas for two days followed by filtration and washing with three 50-mL portions of acetone to remove the solid materials. The combined filtrate was washed with saturated aq. sodium chloride in a 500 mL separatory funnel three times and dried over sodium sulfate for 12 hours. After the removal of drying agent and solvent, the crude product was purified by distillation under the reduced pressure to collect the fraction boiling at 80–83° C./$10^{-2}$ torr. A total of 23.5 g of colorless liquid containing 3,5-di(2-bromotetrafluoroethoxy) benzenesulfonyl fluoride was obtained. The $^{19}$F NMR spectrum of this sample showed that the amount of hydrogen by-product was around 4%.

Preparation of 3,5-di(trifluorovinyloxy)benzenesulfonyl fluoride

Into a 100 mL round bottom flask in a dry box were placed 5.41 g of the 3,5-di(2-bromotetrafluoroethoxy) benzenesulfonyl fluoride, 0.5 g (0.005 mol) of copper(I) chloride and 0.65 g (0.01 mol) of activated zinc powder. Then 15 mL of well-dried acetonitrile was added to the flask. The mixture was stirred at 110° C. under dry nitrogen gas for 2 days, followed by taking a sample for $^{19}$F NMR to monitor the progress of the reaction. The spectrum of this sample showed that all of starting material had converted. After being cooled to room temperature, 75 mL of methylene chloride was added to the flask and the organic layer was stirred at room temperature overnight followed by filtration to remove the salt. The combined organic layer was washed with saturated sodium chloride water solution in a 500 mL separatory funnel three times and dried over sodium sulfate overnight. After the removal of the drying agent, the filtrate was refluxed with 5 g of active carbon for 1 day. After being cooled down to room temperature, the mixture was filtered to remove active carbon and the solvents were evaporated off under the reduced pressure. The crude product was purified first by recrystallization and then by column chromatography (silica gel, 70–230 mesh) using 2 parts by volume of petroleum ether to 1 part by volume of chloroform. A total of 2.5 g of 3,5-di(trifluorovinyloxy) benzenesulfonyl fluoride product was obtained as a transparent liquid in about 50% yield.

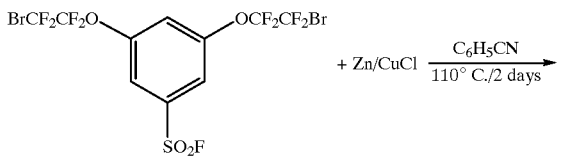

Example 6
Preparation of 4-trifluorovinyloxybenzene sulfonyl fluoride

In a 500 mL round-bottom flask 40.0 g (0.173 mol) of 4-hydroxybenzenesulfonic acid, sodium salt dihydrate (Aldrich Chemical Co., Milwaukee, Wis.) was dissolved in 200 mL of $H_2O$. To this solution, 124 mL of KOH (1.44M) solution was added. The water was removed by rotoevaporation and the remaining salt was dried at $10^{-2}$ torr for 24 hours at 150° C. The salt was placed in a 300 mL Parr autoclave with a magnetic stir bar. Then 200 mL of DMSO, dried over 4A molecular sieves, and 45.4 g (0.175 mol) of $BrCF_2CF_2Br$ was added. The autoclave was sealed and heated to 60° C. for 48 hours. The solvent was removed and the remaining solid was dried under vacuum ($10^{-2}$ torr) at 150° C. for 24 hours.

To the dry solids, 80 mL of sulfolane, and 100 mL of $CH_3CN$ were added and allowed to stir for 10 minutes. To this mixture, 65 mL (0.698 mol) of $POCl_3$ was added. The reaction mixture was heated to 75° C. for 1.5 hours. It was allowed to cool to room temperature and placed in an ice bath. Using an addition fimnel, 150 mL of $H_2O$ was slowly added drop by drop. This mixture was allowed to stir in the ice bath for an additional 10 minutes. The organic layer and aqueous layer were separated using a 500 mL separatory funnel. The product was then distilled under vacuum at $10^{-2}$ torr from the organic layer at 110° C. A total of 36 g of product was collected, resulting in a 56% overall yield of 4-(2-bromotetrafluoroethoxy)benzenesulfonyl chloride ($CBrF_2CF_2$—O—Ph—$SO_2Cl$).

Using a Meeker burner, 20 g (345 mmol) of KF was dried in a ceramic evaporating dish for 4 hours. In a 250 mL round-bottom flask the KF, 36 g (97 mmol) of the $CBrF_2CF_2$—O—Ph—$SO_2Cl$, and 150 mL of acetonitrile were added and allowed to stir for 12 hours at room temperature. The product was vacuum distilled ($10^{-2}$ torr) at 80° C. giving 28 g, for an 81% yield.

In a 250 mL Parr bomb equipped with a stir bar, 28 g (78.9 mmol) of the $CBrF_2CF_2$—O—Ph—$SO_2Cl$ was added with 20 g (315.4 mmol) of zinc and 150 mL of acetonitrile. The bomb was sealed and heated, with stirring, to 120° C. for 16 hours. On cooling, the solution was filtered by vacuum suction to remove the excess zinc. Vacuum distillation ($10^{-2}$ torr) at 65° C. gave 14.2 g of product (6A) in a 70% yield.

(6A)

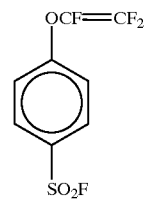

Preparation of TVESF

In a three neck 25 mL flask, purged with nitrogen and equipped with a magnetic stir bar, 1.0 g (1.83 mmol) of monomer 6B (prepared as described, for example, in U.S.

Pat. No. 5,159,038, Example 10, herein incorporated by reference) was placed, followed by 1.0 g (3.9 mmol) of monomer 6A. The solution was stirred for 1.5 h at 160° C., at which time it was noticed that the product had become a solid. The product was dried under vacuum ($10^{-2}$ torr) at 120° C. overnight to remove any dimer and excess monomer 1. A total of 1.2 g of pure product (6C) was collected and ground into a fine powder giving an 82% yield. Analysis by $^{19}$F NMR showed that monomer 6C had oligomerized where an average value for n is 3, and $^1$H NMR showed that for every monomer 6B, there was one monomer 6A that had reacted with it.

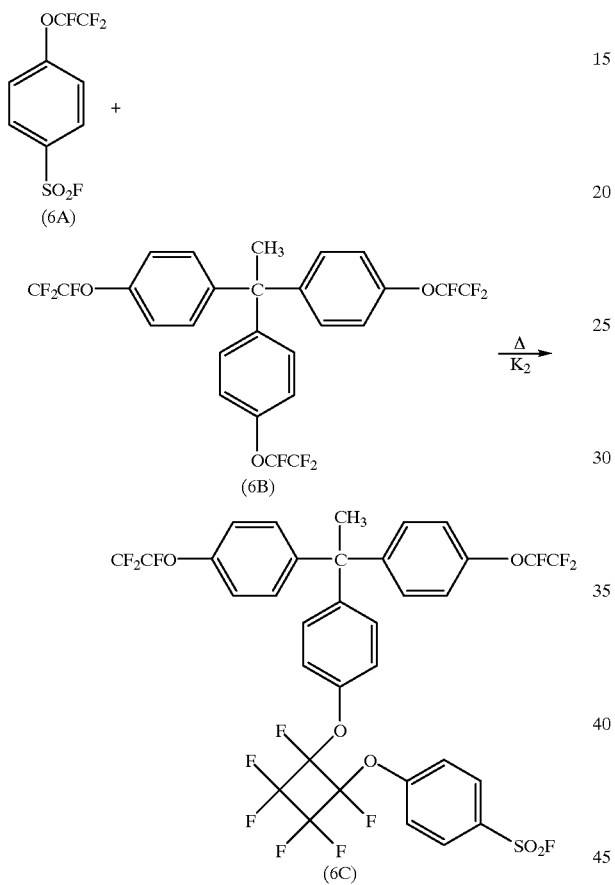

Example 7

Preparation of 4-trifluorovinyloxybenzene sulfonyl chloride

In a 3-neck 250 mL round-bottom flask purged with nitrogen, 20 g (79 mmol) of 4-bromo benzene trifluorovinyl ether (supplied by Dow Chemical) was added to 50 mL of dry ether. The solution was cooled to −80° C. Over 30 minutes, 61.7 mL (78.9 mmol) of 1.28M t-butyl lithium was slowly added by syringe. The solution was allowed to stir for 2 hours at −80° C. Then, 22 g (186.4 mmol) of $FSO_2Cl$ was added from a pressurized glass tube fitted with a glass-Teflon valve. The mixture was stirred at −80° C. for 10 minutes. Then, as the mixture was flash warmed in air, 50 mL of deionized water was added to the flask to neutralize any remaining lithium intermediate. The mixture was then allowed to warm to 22° C. and stirred for 10 minutes. The organic and aqueous layers were then separated using a separatory funnel. The product was vacuun distilled ($10^{-2}$ torr) at 100° C. giving 14 g of product 7A in a 65% yield.

Preparation of TVES-Cl

In a two neck flask purged with nitrogen 5.0 g (18.4 mmol) of monomer (7A) and 5.0 g (9.2 mmol) of monomer 6B (prepared as described, for example, in U.S. Pat. No. 5,159,038, Example 10, incorporated herein by reference) were added. The neat mixture was heated to 160° C. for 1.5 hours. The flask was cooled to room temperature and washed with excess methanol to remove remaining monomer 7A. The remaining product was filtered by vacuum suction giving 6.0 g and 80% yield. Analysis using $^{19}$F NMR and GPC showed that monomer 7B had an average n of 3. and $^1$H NMR results showed conclusive evidence that for every monomer 6B, one equivalent of monomer 7A had reacted with it.

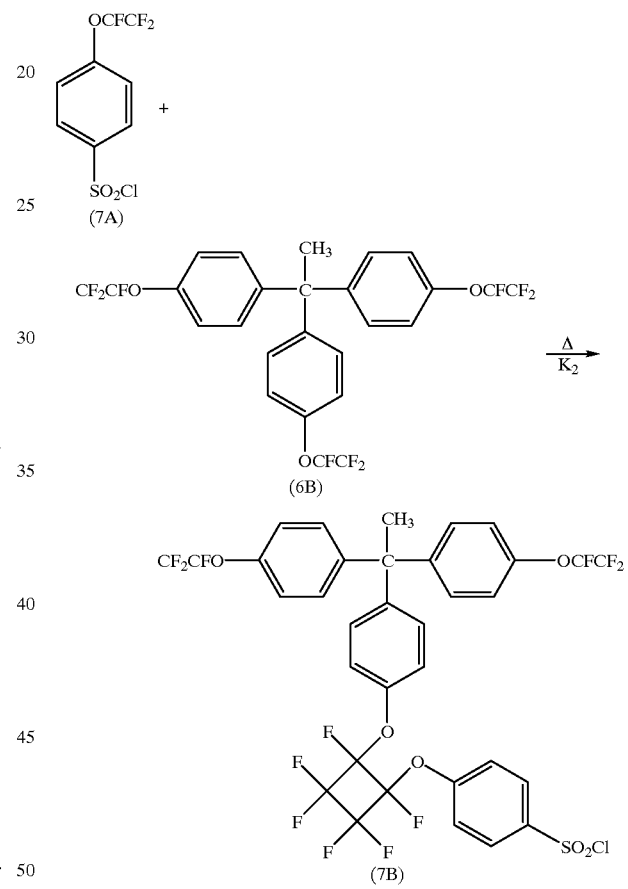

Various modifications and alterations of this invention will become apparent to those skilled in the art without departing from the scope and principles of this invention. It should be understood that this invention is not to be unduly limited to the illustrative embodiments set forth hereinabove. All publications and patents are herein incorporated by reference to the same extent as if each individual publication or patent was specifically and individually indicated to be incorporated by reference.

We claim:

1. A monomer having the formula A—B, wherein A is represented by Formula I:

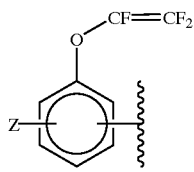
(I)

wherein B is selected from —OCF=CF$_2$, and —A;

wherein the orientation of B is meta or para to the trifluorovinyloxy group of A when B is —OCF=CF$_2$;

wherein, when B is A, the bond joining the A groups is para to the trifluorovinyloxy group of each A; and wherein each Z is independently selected from —SO$_2$F, —SO$_2$Cl, —SO$_3$H, —SO$_2$—N(M)—SO$_2$CF$_3$, and —SO$_2$—N(M)—SO$_2$R$_f$; wherein M is any suitable cation and R$_f$ is a C1 to C10 fluorocarbon or fluorinated ether group.

2. The monomer of claim 1 wherein B is —OCF=CF$_2$.
3. The monomer of claim 1 wherein B is A.
4. The monomer of claim 1 wherein Z is —SO$_2$F.
5. The monomer of claim 1 wherein Z is —SO$_2$—N(M)—SO$_2$CF$_3$.
6. The monomer of claim 1 wherein Z is —SO$_2$—N(M)—SO$_2$R$_f$.
7. The monomer of claim 1 wherein Z is —SO$_2$—N(M)—SO$_2$CF$_3$ and B is —OCF=CF$_2$.
8. The monomer of claim 1 wherein Z is —SO$_2$F and B is —OCF=CF$_2$.
9. The monomer of claim 1 wherein B is A and each Z is —SO$_2$—N(M)—SO$_2$CF$_3$.
10. A monomer of Formula II:

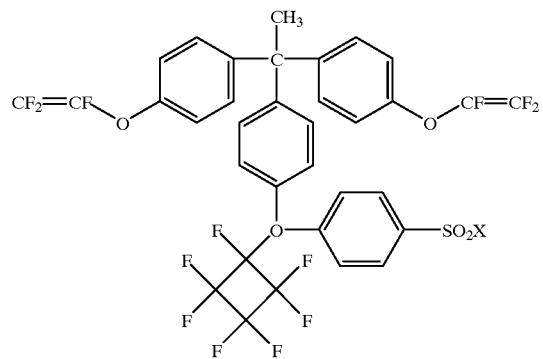
(II)

wherein X is F, Cl, or N(M)SO$_2$R$_f$, wherein M is any suitable cation and R$_f$ is a C1 to C10 fluorocarbon or fluorinated ether group.

11. The monomer of claim 9 wherein X is F.

* * * * *

UNITED STATES PATENT AND TRADEMARK OFFICE
CERTIFICATE OF CORRECTION

PATENT NO.    : 6,268,532 B1
DATED         : July 31, 2001
INVENTOR(S)   : DesMarteau et al.

It is certified that error appears in the above-identified patent and that said Letters Patent is hereby corrected as shown below:

Column 2,
Line 53, delete "09/589,522" and insert in place thereof -- 09/587,522 --

Column 4,
Line 50, delete "fill" and insert in place thereof -- full --
Line 57, delete "fimnel" and insert in place thereof -- funnel --
Line 67, delete "fmal" and insert in place thereof -- final --

Column 16,
Line 30, delete "fimnel" and insert in place thereof -- funnel --

Column 17,
Line 66, delete "vacuun" and insert in place thereof -- vacuum --

Signed and Sealed this

Twenty-eighth Day of January, 2003

JAMES E. ROGAN
*Director of the United States Patent and Trademark Office*